United States Patent [19]
Mody et al.

[11] Patent Number: 6,017,516
[45] Date of Patent: Jan. 25, 2000

[54] PHARMACEUTICAL DENTAL FORMULATION FOR TOPICAL APPLICATION OF METRONIDAZOLE BENZOATE AND CHLORHEXIDINE GLUCONATE

[75] Inventors: Shri Shirish Bhagwanlal Mody; Pranabh Dinesh Mody; Madhukant Mansukhlal Doshi, all of Maharashtra, India

[73] Assignee: Lekar Pharma Limited, Mumbai, India

[21] Appl. No.: 08/962,099

[22] Filed: Oct. 31, 1997

[51] Int. Cl.[7] ............................... A61K 7/24; A61K 7/16
[52] U.S. Cl. ................................. 424/55; 424/49
[58] Field of Search .................................. 424/49

[56] References Cited

U.S. PATENT DOCUMENTS 5,143,934  9/1992  Lading et al. ........................... 514/396
5,262,164  11/1993  Damani et al. ......................... 424/422

OTHER PUBLICATIONS

V. Pedrazzoli et al J. Clin. Periodont. 1992:19:715–722 "Comparative Clinical . . . ".
J. Ainamo et al J. Clin. Periodont. "Clinical Responses . . . " 1992:19:723–729.
D.F. Hoyos et al Brit. dent. J. 1977, 142, 366.

*Primary Examiner*—Peter F. Kulkosky
*Attorney, Agent, or Firm*—McAulay Nissen Goldberg Kiel & Hand, LLP

[57] ABSTRACT

A pharmaceutical dental formulation of therapeutically effective amounts of metronidazole benzoate and chlorhexidine gluconate is described. The formulation also includes a gelled hydrophilic and water-dipersible polymer having free carboxylic groups, an aqueous base, a penetration enhancer and a chelating agent. The formulation is for topical application in the form of an aqueous gel in the treatment of periodontal diseases including gingivitis, stomatitis, Apthous ulcers and post-extraction infection.

17 Claims, No Drawings

PHARMACEUTICAL DENTAL FORMULATION FOR TOPICAL APPLICATION OF METRONIDAZOLE BENZOATE AND CHLORHEXIDINE GLUCONATE

TECHNICAL FIELD

The present invention relates to the pharmaceutical dental formulation for topical application in the form of aqueous gel suitable for the treatment of periodontal diseases which mainly include gingivitis, stomatitis, apthous ulcers, post extraction infections.

BACKGROUND OF INVENTION

The periodontal disease as used herein is a broad term used to describe those diseases which attack the gingiva and the underlying alveolar bone supporting the teeth. Two common periodontal diseases are gingivitis (inflammation of the gingiva) and periodontitis manifested by progressive resorption of alveolar bone, increasing mobility of the teeth and loss of the teeth at advanced stage). Periodontal disease is characterised by one or more of the following inflammation of the gingiva, formation of periodontal pockets bleeding and/or pus discharge from the periodontal pockets, resorption of alveolar bone, loose teeth and loss of teeth. This disease is generally considered to be caused by/associated with bacteria which are generally present in dental plaque which forms on the surface of the teeth and in periodontal pocket. Inflammation of the soft tissues (gingivae) around teeth is referred to as gingivitis and may be caused by microbial infection. In the case of progressive infection, direct microbial actions as well as the production of tissue-destructive enzymes such as collagenase, with or without stimulation of host tissue-destructive enzyme activity by the infectious agents can lead to destruction of supporting tissues around the teeth, a condition referred to as periodontitis (Klausen et al, 1991). The subgingival microbiota associated with these peridental conditions may be comprised of multiple species and may change during the course and progression of the dental infections. Gram (−ve) anaerobic bacteria in particular, are known to play an essential role.

It is known fact that the mouth is colonized by microorganisms a few hours after birth, mainly by aerobic and facultative anaerobic organisms. The eruption of teeth allows the development of a complex eco-system of microorganisms (>300 species have been identified). In healthy mouth,it depends on maintaining an environment in which these organisms exist without damaging oral structures. The microorganism involved in oral infections (Oxford Handbook of Clinical Dentistry, 2nd Edition) are as follows:

*Streptococcus mutans*: Aerobic. Synthesizes dextran. Colony density on tooth surface plaque rises to >50% in presence of high dietary sucrose. Able to produce acid from most sugars. The most important organism in the aetiology of dental caries.

*Streptococcus sanguis*: Accounts for half the streptococci isolated from saliva. Inconsistent producer of dextran.

*Streptococcus milleri group*: Common isolates from dental abscesses, also implicated in abscess formation at other sites in the body. Three recognized species.

Lactobacillus: Secondary colonizer in caries (mainly dentine).

*Porphyromonas gingivalis*: Obligate anaerobe. A member of the 'black pigmented bacteroides' group which is associated with rapidly progressive periodontitis. Others include *Prevotella intermedia* and *P. denticola*.

Fusobacterium: Obligate anaerobes. Originally thought to be principal pathogens in Acute ulceration gingivitis (AUG). Remain a major periodontal pathogen as a collective group. The terminology for specific organisms is confusing and unimportant.

*Borrellia vincenti*: (refringens) The largest oral spirochaete and once thought to be the major co-pathogen in AUG. This disease is best now thought of as simply an anaerobic, fusospirochaetal complex infection.

*Actinobacillus actinomycetemcomitans*: Microaerophilic, capnophillic, gram negative rod. Found particularly in juvenile periodontitis and rapidly progressive periodontitis.

*Actinomyces israelii*: Filamentous organism, major cause of actinomycosis, a persistent rare infection which occurs predominantly in the mouth and jaws and the female reproductive tract. Implicated in root caries.

*Candida albicans*: Yeast-like fungus famous as an opportunistic oral pathogen, probably carried as a commensal by most people.

Spirochaetes: Obligate anaerobes much implicated in periodontal disease, present in virtually all adult mouths, Borrelia, Treponema, and Leptospira all belong to this family.

It is a known fact that for treating periodontal diseases, antimicrobials are used. Penicillins in general are highly effective antimicrobial compositions against anaerobic bacteria. Some penicillins, such as Amoxicillin, have antimicrobial activity against anaerobic bacterial and some gram (−ve) bacterial species. Nevertheless, both Penicillin G and Amoxicillin have been shown to be ineffective against bacterial species important in peridental infections, such as P.gingivitis.

Also, Tetracyclines are impressively broad spectrum antimicrobial agents with activity against a wide range of bacterial and non bacterial species. However, tetracycline have a number of disadvantages relative to use in dental medicine which are related to their bacteriostatic mechanism of action and broad spectrum activity. For example, the rapid emergence of bacterial strains which are resistant to tetracyclines and the occurence of overgrowth of unsusceptible pathogens, such as Candida during treatment constitute serious limitations to the use of this class of anti-microbials in the treatment or prevention of dental infections leading to teeth loss. The broad spectrum of activity of tetracyclines can result in superinfection of the diseased tissue by bacteria which are unsusceptible to its antimicrobial action, and can also result in opportunistic infection of healthy tissues. Prolonged or frequent treatment courses with broad spectrum antimicrobials enable superinfecting organisms to persist in the sub-gingival microbial community over extended periods of time, contributing to therapeutic failure.

Periodontal diseases can also be treated with a compositon comprising of Metronidazole Benzoate 25% and with a composition comprising of Chlorhexedine gluconate individually.

METRONIDAZOLE

Metronidazole ie 1-(B-hydroxyethyl)-2-methyl-5-nitroimidazole, belongs to the class of substituted alkyl imidazole derivatives and are useful as antimicrobial agents. The term 'metronidazole' as used in this specification and claims, in-cludes not only 1-(2-hydroxyethyl)-2-methyl-5-nitroimidazole, but also those analogs and derivatives of metronidazole (salts, esters, etc) which are soluble in the aqueous or oil phases of the compositions described herein and which exhibit therapeutic activity when applied as taught by the present invention.

Metronidazole has a 5-nitroimidazole derivative with activity against anaerobic protozoa and anaerobic bacteria. It also has a radio sensitizing effect on hypoxic tumor cells.

A mechanism of action of Metronidazole is thought to involve interference with DNA by metabolite in which the nitro group of metronidazole has been reduced (Martindale—The Extract Pharmacopoeia, 31st Edition).

Although, Metronidazole has been used therapeutically in various disorders, the long term use of oral metronidazole in chronic condition like periodontal disease may be associated with certain side effects such as gastro-intestinal disturbances, nausea and an unpleasant mettalic taste, anorexia and vomiting, Diarrhoea, dry mouth, a furried tongue and glossitis may also occur which are well-known. Similarly the role of systemic administration of antibacterial therapy has its own drawbacks. Therefore a topical formulation of metronidazole is an essentiality for periodontal disease.

Metronidazole Benzoate:

Metronidazole Benzoate is benzoyl derivative of metronidazole. Metronidazole Benzoate is hydrolysed into metronidazole by esteraces present in the GEF (Barett 1972, Cimagon 1974).

Barret A J (1972) Lyosomes. A Laboratory Handbook Dingle J.T(ed) Amsterdam, North Holland Publishing Company.Cimagani G.(1974) Monographs in Oral Science Myers, H. M. (ed) p.35,6514 47,71 Basee:S Karser.

A dental composition comprising of Metronidazole Benzoate 25%, dentel gel used for gingivitis and periodontal diseases, and its topical use seems to be as effective as conventional mechanical therapy in the treatment of adult periodontitis (J.Clin.Periodontal 1992:19;715–722).

Metronidazole Benzoate 25% dental gel when applied sub gingivally reduced significantly Probing Pocket Debth (PPD) and bleeding on probing (BOP) significantly as compared to control (J.Clin. Periodontal 1992: 19, 723–729).

The limitations and disadvantages associated with the use of Metronidazole Benzoate 25% dental gel is as follows:
1. It is used subgingivally so that it reaches sulcus. This requires a special injector and the procedure can be done by dental surgeon only.
2. Patients cannot use it himself.
3. Metronidazole has got strong action against anaerobic bacteria and no action against aerobic bacteria.

Similarly a dental composition consisting of Chlorhexidine Gluconate in various strengths of 0.1% to 16 in the form of topical preparations also used for periodontal diseases, has been reported in Br.Dental J 1977; 142; 366–369.

CHLORHEXIDINE

Chlorhexidine is a bis biguanide disinfectant which is effective against wide range of vegetative gram-positive and gram-negative bacteria. Chlorhexidine is also active against some virus and fungi. Chlorhexidine in various strengths from 0.1% to 1% has been used in dentistry in order to take care of periodontal disease in form of gel or solution or paste. Chlorhexidine has much more potent action on aerobic bacteria.

Chlorhexidine being a antiseptic and disinfectant, has bacterialcidal and bacteriostatic action against a wide range of bacteria.

Thus taking into consideration that metronidazole has no action against aerobic bacteria and Chlorhexidine has more potent action on aerobic bacteria, if used individually will not be able to cover both anaerobic and aerobic bacteria.

The lack of success in providing a solution to the problems associated with the use of antimicrobial agents and other compositions available in the market expose the continued need for effective treatment of these dental infections and this has attempted the inventors to device such a formulation comprising of antimicrobial agent such as Metronidazole Benzoate and biguanide disinfectant such as chlorhexidine gluconate which is found to be effective against wide range of gram (+ve) and gram (−ve) bacteria. Also, this formulation can be applied by the patient himself twice daily on gingival surface. There is no necessity of using injector. Once applied to gingival surface, active metronidazole enters the gingival pocket and reaches periodontal membrane where it exerts anaerobicidal action.

It is a object of this invention to provide a pharmaceutical formulation in the combination of metronidazole benzoate and chlorhexidine gluconate in the form of aqueous gel having the effect on aerobic and anaerobic bacteria in peridontal disease and this combination has been found to be therapeutically advanced over either metronidazole benzoate or chlorhexidine gluconate individually and easier/patient friendly in application also.

BRIEF DESCRIPTION OF THE INVENTION

The present invention provides the pharmaceutical dental formulation for topical application in the form of aqueous gel suitable for the treatment of periodontal diseases.

The present formulation provides the method for the prophylactic or curative treatment to individuals affected with
1. Chronic gingivitis
   a. Chronic Edematous Gingivitis
   b. Chronic Hyperplastic gingivitis
   c. Chronic atrophic gingivitis
2. Acute gingivitis
   a. Acute ulcerative gingivitis (Vincent's gingivitis)
3. Chronic Periodontitis
4. To prevent post extraction infections (Dry Sockets)
5. Recurrent Apthous Stomatitis (Ulcer)
6. Dental Pain due to infection
1. Chronic gingivitis is an inflammation of the gingival tissue. It is not associated with bone resorption or apical migration of the junctional epithelium, falls pockets of less than 2 mm size can occur due to hyperplasia of gingiva. The gingivitis is the results of low grade infection because of the presence of gram-negative anaerobes giving rise to inflammatory changes.
2. Acute Gingivitis is also known as Vincent's gingivitis is characterized by painful papulary ulcers which bleeds readily.

Many anaerobic bacteria have been said to be involved in pathogenesis of acute ulceration gingivitis (AUG) such as borellia, vincent's fuso-bacteriam fusiformis, bacteroid melanogenices and treponema species.
3. Chronic Periodontitis can be regarded as a progression of the combination of infections and inflammation of gingivitis into a deep tissues of the periodontal membrane. It is characterized by breakdown of periodontal fibre bundles and resorption of alveolar bone and apical proliferation of junctional epithelium.
Chronic periodontitis develops due to infections with gram-negative anaerobic rods and spirochaetes.
4. Dry Socket is being described as a painful tooth socket following recent extractions and accompanied by partial or total loss of the blood clotbleed. Anaerobic bacteria are implicated in the pathogenesis of dry socket.
5. Recurrent Apthous Stomatitis (Ulcer) Apthous ulcer is well-known condition occurring in 25% of population. Usually they present with one group of 1 to 6 ulcer. Usually they last for 10 days and heal without scarring. The exact etiology is not known. They get painful due to super infection.

According to the present invention there is provided a pharmaceutical dental formulation in the form of a gel for topical application comprising of:
1) a therapeutically effective amount of metronidazole benzoate and chlorhexidine gluconate as therapeutic ingredients;
2) a gelled, hydrophillic and water-dispersible polymer having free carboxylic groups which is a polyacrylic acid polymer having a molecular weight in the range of about 1,250,000 to about 4,000,000 daltons.
3) an aqueous base for the said metronidazole and chlorhexidine gluconate;
4) a chelating agent;
5) a penetration enhancer.
6) a flavouring agent and a sweetening agent;

Ingredients present in the topical oral carrier of the present invention are suitable for administration to the oral cavity of a human and are compatible with one another used in topical composition of the present invention. Metronidazole Benzoate present in the composition is in the range of 0.5% to about 3%, preferably between 0.8 to 1.6% by wt. based on total weight of the said composition.

Chlorhexidine gluconate is a component of the topical oral carriers of the composition of the present invention. Chlorhexidine gluconate is in the range of about 0.01% to 0.5%, the prefered range is 0.01 to about 0.1% by weight based on total weight of the said composition.

The polymer present in the composition is in the range of about 0.2% to about 7% by wt. based on the total wt. of the said composition. The results are better with polymer 1.5% by wt. based on the total wt. of the said composition.

The penetration enhancer present in the composition is in the range of about 2% to about 10% by wt. based on the total wt. of the said composition. The better results are obtained with penetration enhancer 0.5 by wt. based on the total wt. of the said composition.

The expression 'chelating agent' as used in this specification refers to Disodium Edetate U.S.P., Edetic Acid, Citric Acid, Disodium Calcium Edetate.

However, Disodium Edetate is preferably used as chelating agent in the gel composition of the present invention in an amount of 0.01% to about 0.1% by wt. and preferably, in an amount of about 0.025% by wt. based on the total wt. of the composition.

The expression 'sweetening agent' as used in this specification refers to Sacchrine Sodium, Aspartame, Dihydrochalcowes, D-tryptophan, acesulfame and cyclamate salts.

The expression 'flavouring agent' as used in this specification refers to Menthol, pepermint oil, spearmint oil, Anise oil and clove oil.

The expression a 'gelled, hydrophillic and water dispersible polymer' as used in the specification refers to Carbomer 940, carbomer 934, Hydroxypropylmethylcellulose, Sodium Carboxymethyl Cellulose.

The expression 'penetration enhancer' as used in this specification refers to Propyleneglycol, Glycerine, Polyethyleneglycols. The preferable penetration enhancer used for the composition is propyleneglycol.

Mechanism of action of combination of metronidazole benzoate and chlorhexidine gluconate of the present composition.

This gel when applied on the affected part, flows and fills out the gingival pocket after application and thereafter comes into contact with the aqueous part of either gingival cravicular fluid or saliva containing esterases. These hydrolyse microbiologically inactive Metronidazole benzoate to free metronidazole and benzoic acid Metronidazole exerts its aerobicidal activity on anaerobic bacteria present in periodontal region.

The pharmaceutical dental formulation in the form of gel may be prepared by a process comprising of the following steps:
(a) dissolve disodium EDTA, Sodium Saccharin and chlorhexidine gluconate in a purified water.
(b) dissolve menthol separately in propylene glycol.
(c) Step (b) is added to step (a).
(d) required quantity of Metronidazole benzoate was added to the mixture and dispersed with continuous stirring.
(e) Carbomer 940 polymer was added to step (d) with continuous stirring to form a uniform viscous gel.
(f) the pH of the gel was adjusted between 5 & 6 by adding 10% NaoH solution and tested by quality Control Dept.

CLINICAL TRIALS

To investigate the effectiveness of the present invention in periodontal diseases, dry sockets and apthous ulcer stomatitis, multicentric controlled clinical trials were carried out in 5 different centres all over India. A total of 170 patients of different age groups were included in the trial.

The methods of preparation were not disclosed to the public and the trials were done in confidence. The results of clinical trials in India is given below:
a) 50 patients having chronic gingivitis were included into study. They were divided into 2 groups of 25 each. One group received scaling as a treatment and other group received scaling plus composition of the present invention, twice a day for 2 weeks. On follow-up it was found that patients maintained on scaling plus the present composition application were recovered faster in respect to bleeding on probing and probing pocket depth. The size of the pocket reduced faster in the present composition group compared to group subjected to scaling. The study shows that application of present composition along with scaling was found to be superior to scaling alone in chronic gingivitis.
b) 40 patients suffering from acute ulcer gingivitis were included in the trial and they were divided into 2 groups. Group one received Chlorhexidine 0.25% gel twice daily and other group received the gel of the present composition twice daily in both the groups thorough debridment was carried out. The group of the present composition showed improvement much faster compared to the group of 0.25 chlorhexidine gel alone. However in both the groups gingivectomy was not required. This study shows that the composition of the present invention is a better choice than chlorhexidine alone.
c) 30 patients suffering from chronic periodontitis were included in the trial. They were divided into 2 groups of 15 each. One group received scaling and chlorhexidine gel 0.25% as a treatment whereas other group receiving scaling plus the present composition. The group received gel of the present composition showed faster improvement in probing pocket depth and bleeding on probing compared to scaling and chlorhexidine.

Taking into consideration above results of the present composition as an adjunct to scaling is superior to scaling and 0.25% chlorhexidine gel in chronic periodontal diseases.
d) 30 patients undergoing extractions of tooth were included in the study. They were divided into 2 groups of 15 each. One group received the gel of the present invention for application twice daily and analgesic whereas other group received only analgesic. The group receiving the present composition did not develop any dry socket whereas the group treated with only antiinflammatory, 5 patients were found to develop dry socket. Therefore, for patients undergoing tooth extraction, the present composition should be routinely used.

e) In a study 20 patients were included suffering from recurrent apthous stomatitis (Ulcer). They were divided into 2 groups of 10 each. 1 group was treated with analgesics and the present composition twice daily and other group was treated with analgesic and 0.25% chlorhexidine gluconate gel only.

The group treated with the present composition showed faster healing of ulcer and relief from pain compared to patients maintained only on analgesic and chlorhexidine gel. The above clinical trials confirms that efficacy of the composition of the present invention in following conditions.

1. Chronic gingivitis
    a. Chronic Edematous Gingivitis
    b. Chronic Hyperplastic gingivitis
    c. Chronic atrophic gingivitis
2. Acute gingivitis
    a. Acute ulcerative gingivitis (Vincent's gingivitis)
3. Chronic Periodontitis
4. To prevent post extraction infections (Dry Sockets)
5. Recurrent Apthous Stomatitis (Ulcer)
6. Dental Pain due to infection The following example is provided to illustrate the present invention and should not be misunderstood to limit the scope of the present invention in any way.

EXAMPLE

A one kg batch of composition of the present invention was prepared as follows:

To 920 ml. of purified water, 0.25 g disodium Edetate (0.025%), 1 g of sodium Saccharin and 2.5 g chlorhexidine Gluconate solution B.P. (0.25%) were added and dissolved. 5 g of Menthol was separately dissolved in 50 g of propylene glycol (5%) and this solution was added to the solution prepared above. 16 g of Metronidazole Benzoate, equivalent to 10 g metronidazole (19%) was then added and dispersed with continous stirring. Carbomer 940, 15 g was then added to the mixture with continous stirring to form a smooth uniform viscous gel. The pH of gel was then adjusted between 5 to 6 with 10% sodium hydroxide solution. The final weight of the gel was adjusted to one kg by addition of distilled water and mixed well.

It is to be understood that the example and embodiments described hereinabove are for the purpose of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

We claim:

1. A phannaceutical dental formulation for topical application in the form of an aqueous gel suitable for the treatment of periodontal diseases which mainly indude gingivitis, stomatitis, Apthous ulcers, and post extraction infection, comprising:

therapeutically effective amounts of metronidazole benzoate and chlorhexidine Gluconate as therapeutic ingredients;

a gelled, hydrophilic and water-dispersible polymer having free carboxylic groups which is a polyacrylic acid polymer having a molecular weight in the range of about 1,250,000 to about 4,000,000 daltons;

an aqueous base for the said metronidazole benzoate and chlorhexidine gluconate; penetration enhancer; a chelating agent; a sweetening agent and a flavouring agent.

2. A pharmaceutical dental formulation in accordance with claim 1, wherein the concentration of said metronidazole benzoate present is in the range of about 0.5% to about 3.0% by weight based on the total weight of said pharmaceutical dental formulation and said chlorhexidine gluconate content present is in the range of 0.01% to 0.5%.

3. A pharmaceutical dental formulation in accordance with claim 2, wherein the concentration of said metronidazole benzoate is at least about 0.8% by weight and said chlorhexidine gluconate is at least about 0.01% by weight based on the total weight of the said pharmaceutical dental formulation.

4. A pharmaceutical dental formulation in accordance with claim 2, wherein the concentration of said metronidazole benzoate present is about 1.6% by weight based on the total weight of said pharmaceutical dental formulation and said chlorhexidine gluconate is from 0.05% to 0.25% by weight based on total weight of said pharmaceutical dental fomulation.

5. A pharmaceutical dental formulation in accordance with claim 1, wherein said gelled, hydrophilic and water-dispersible polymer is selected from the group consisting of carbomer 940, carbomer 934, Hyroxypropylmethylcellulose, and sodium carboxymethylcellulose in a range of about 0.2% to about 7.0 percent by weight based on the total weight of said pharmaceutical formulation.

6. A pharmaceutical dental formulation in accordance with claim 5, wherein said gelled, hydrophilic and water dispersible polymer is carbomer 940.

7. A pharmaceutical dental formulation in accordance with claim 5, wherein said gelled hydrophilic and water-dispersible polymer is present in an amount of about 1.5% by weight based on the total weight of said pharmaceutical dental formulation.

8. A pharmaceutical dental formulation in accordance with claim 1, wherein the penetration enhancer is selected from the group consisting of propylene glycol, glycerin, and polyethylene glycols.

9. A pharmaceutical dental formulation in accordance with claim 8, wherein said penetration enhancer is propylene glycol present in a range of about 2% to about 10% by weight based on the total weight of said pharmaceutical dental formulation.

10. A pharmaceutical dental formulation in accordance with claim 9, wherein said penetration enhancer is present in an amount of about 5% by weight based on the total weight of the pharmaceutical dental formulation.

11. A pharmaceutical dental formulation in accordance with claim 1, wherein said chelating agent is selected from the group consisting of Disodium Edetate USP, Edetic acid, Citric acid, and Disodium Calcium Edetate.

12. A pharmaceutical dental formulation in accordance with claim 11, wherein said chelating agent is Disodium Edetate present in a range of about 0.01% to about 0.1 percent by weight based on the total weight of said pharmaceutical digital formulation.

13. A pharmaceutical dental formulation in accordance with claim 12, wherein said chelating agent is present in an amount of about 0.025% by weight based on the total weight of the pharmaceutical digital formulation.

14. A pharmaceutical dental formulation in accordance with claim 1, wherein said sweetening agent is selected from the groups consisting of saccharine sodium, aspartame, dihydrochalcones, D-tryptophan, acesulfame and cyclamate salts.

15. A pharmaceutical dental formulation in accordance with claim 14, wherein said sweetening agent is saccharine sodium.

16. A pharmaceutical dental formulation in accordance with claim 1, wherein said flavouring agent is selected from the group consisting of menthol, peppermint oil, spearmint oil, Anise oil and clove oil.

17. A pharmaceutical dental formulation in accordance with claim 16, wherein said flavouring agent is menthol.

* * * * *